United States Patent [19]

Brownlee et al.

[11] 4,451,363
[45] May 29, 1984

[54] CARTRIDGE FOR LIQUID CHROMATOGRAPH

[75] Inventors: Robert Brownlee, Los Altos Hills; Jeremy W. Higgins, Los Altos, both of Calif.

[73] Assignee: Brownlee Labs Inc., Santa Clara, Calif.

[21] Appl. No.: 354,394

[22] Filed: Mar. 3, 1982

[51] Int. Cl.³ ............................................. B01D 13/08
[52] U.S. Cl. .................................... 210/198.2; 55/386
[58] Field of Search ................. 210/356, 198.2; 55/386

[56] References Cited

U.S. PATENT DOCUMENTS

| | | | |
|---|---|---|---|
| 3,682,315 | 8/1972 | Haller | 210/198.2 |
| 3,791,522 | 2/1974 | Eisenbeiss et al. | 210/198.2 |
| 4,228,007 | 10/1980 | Rausch et al. | 210/198.2 |
| 4,313,828 | 2/1982 | Brownlee | 55/386 X |
| 4,389,313 | 6/1983 | Charney et al. | 210/198.2 |

Primary Examiner—John Adee
Attorney, Agent, or Firm—Robert B. Block

[57] ABSTRACT

A replaceable cartridge column for use in high pressure liquid chromatograph pumping systems including a solid tube having a small bore therethrough carrying a packing material. The tube and terminated by a recess at each end which extends from the rim at the end of the tube inwardly and in communication with the bore. A plastic seal plug is disposed in the recess at each end to extend slightly beyond excess the length of the tube when so disposed and carries at its outer end a coaxial frit filter. The recess is provided with a flat bottom and the plastic plug has a corresponding bottom constructed to be positioned in face-to-face sealing opposition to fluid leakage and having further a flat sealing surface at its other end to engage a sealing surface of an end fitting of the liquid chromatographic pumping system and to provide a first, primary seal therewith independent of the rim of the column tube.

6 Claims, 3 Drawing Figures

U.S. Patent May 29, 1984 4,451,363
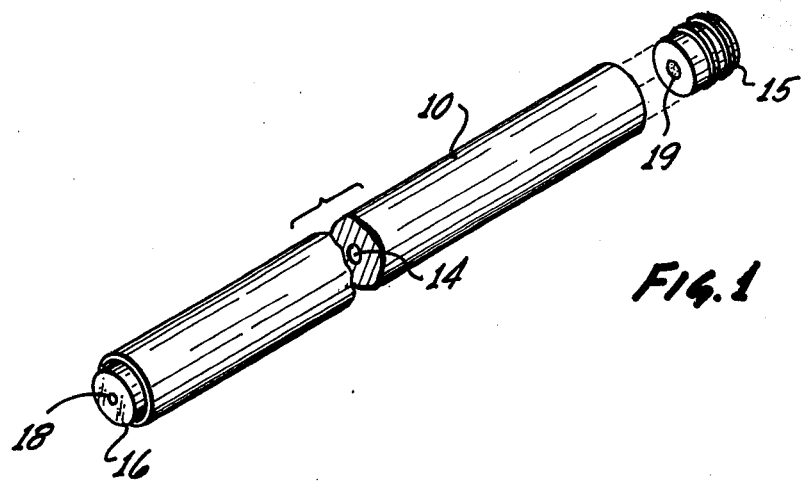
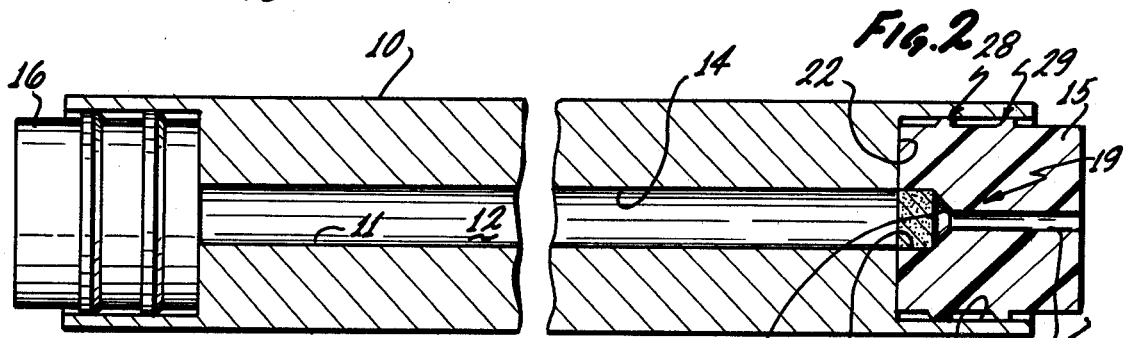
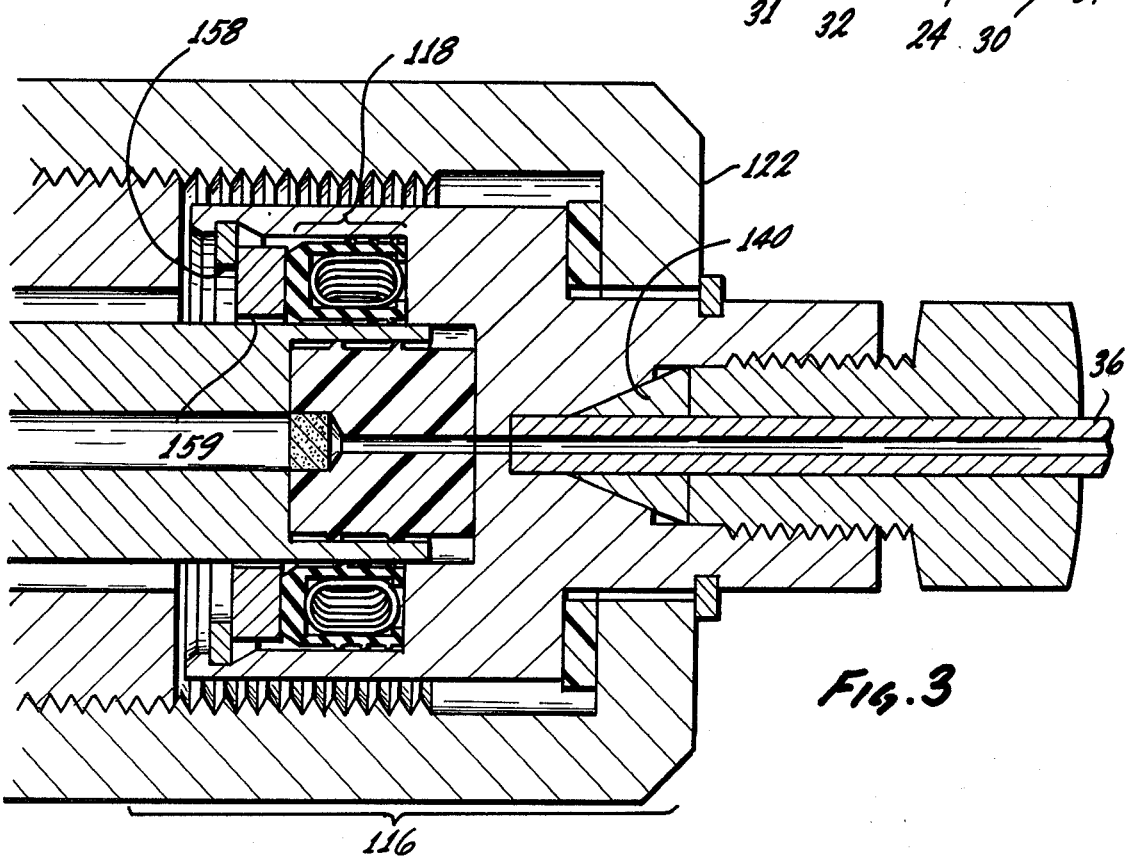

CARTRIDGE FOR LIQUID CHROMATOGRAPH

CROSS REFERENCES TO RELATED APPLICATION

Reference is made to our related application U.S. Ser. No. 354,395 entitled HIGH PRESSURE SEAL AND COUPLING, filed Mar. 3, 1982.

BACKGROUND OF THE INVENTION

This invention relates to replaceable cartridges for liquid chromatographs and more particularly to a replaceable column cartridge adapted to be easily and readily coupled into or removed from the high pressure liquid sample line of the liquid chromatograph. The presently described tube is of the microbore type and is particularly adapted for use as a replacement cartridge in liquid chromatograph systems of the type disclosed in U.S. Pat. No. 4,313,828 entitled High Pressure Tubing Coupler issued Feb. 2, 1982.

In the cross-referenced patent and application, an end fitting was described as arranged with a body portion for closely fitting to a column in the form of a tubing and having an end sealed by a plug which fits over the rim at the end of the tubing. A bell portion is provided in the body of the seal for receiving a hydraulic secondary seal for surrounding and coupling between the bell and the tubing column outer wall and by which secondary leakage under high pressure operation fills and hydraulically operates the seal. The primary seal remains the plug between the column end wall or rim and the bottom of the recess of the end fitting the latter being coupled to a capillary input and output lines of the LC system. Suitable means is provided for placing the column in compression so as to obtain a first sealing effect. The arrangement is such that when the compression means are taken up, the column and first seals are compressed together in the region of the peripheral rim of the column to provide the seal.

While the foregoing arrangement has been found to be very satisfactory, the details for carrying out the construction of the column so as to prevent any easy and reliable removal and replacement particularly adapted to microbore columns is needed. Furthermore, where at the packed bed length is exceedingly small, say about one centimeter, and the diameter is reduced to about two millimeters, the overall dimensioning is approaching a stage wherein redesign is appropriate. It is necessary to so reduce the overall length of guard columns so as to reduce the variance found in the operation of the column to less than about 20 microliters (squared). Thus it is now found that the diameter of the end seal has been favorably reduced by providing the seal in the smaller overall diameter apart. More particularly instead of the "T" section having a top enlarged end which overlaps the end of the tube, it is now found more satisfactory to supply a recess in the end of the tube in communication with the tube floor and to fit a plug into this recess to effect a seal. By doing so it is found the seal immediately adjacent the bore is satisfactory and that the turbulance is reduced by employing a smaller diameter frit and seal bore so that flow and dead volume are reduced proportionally. A further occasional difficulty arose in the prior construction in that, when disassembled, there was a tendency for the plug to fall out of the column with attendant loss of packing effectively destroying its usefullness. By employing the plug design and seal of the present invention it has been found that this tendency is substantially reduced.

SUMMARY OF THE INVENTION AND OBJECTS

In general, it is an object of the present invention to provide a replaceable cartridge and seal which will overcome the above limitations and disadvantages.

A further object of the invention is to provide a cartridge of the above character which is easily removed from the liquid chromatograph for replacement or other purposes, which does not disassemble, and which is relatively simple in design and construction.

A further object of the invention is to provide a cartridge of the above character which easily adapts to a concentric design having a low turbulence factors and in which the seals are effected on surfaces immediately proximate and surrounding the bore.

A further object of the invention is to provide a cartridge of the above character in which a frit filter is readily incorporated into a low turbulence design which can be easily installed.

A further object of the invention is to provide an improved cartridge of the above character which is interchangeable with previously designed cartridges of similar character as disclosed in the cross-reference patents and which preserves an end-to-end first seal arrangement in direct opposition to leakage forces.

The foregoing objects are achieved in accordance with the present invention by providing a cartridge comprising an elongated tube which may have an overall outer diameter the same as tubes of similar character heretofore available. The tube is provided with an internal bore which extends along its length concentrically and it opens at each end into a concentric cylindrical recess. The recess is provided on its inward side with a flat bottom. A plug is designed of generally cylindrical character for an interference fit within each recess and is dimensioned to extend slightly beyond the end of the tube, i.e., as mentioned to have a length slightly greater than the depth of the recess so that when all assembled the tube may be placed in end-to-end compression and a seal force developed by deformation or compression directly upon the plug and between it and the bottom wall of the recess and the end walls of the plug and the inner end wall of the fitting into which it is shoved. The plug is thus faced with two parallel opposite faces and has an internal bore, the plug bore corresponding to that of the bore of the tube, the latter of which contains packing material. It is the function of the plug to retain packing material in the tube, to serve as a holder for a frit filter, and to provide the sealing interface between the column tube and the end fitting into which it is positioned. The seal force provided is a first seal and appears at the bottom wall of the recess to the plug and from the top of the plug to the bottom of the end fitting. In this way, the leakage is sealed by forces in exact angular opposition to the leakage forces and is independent of the rim of the tube and is proximate to the bore itself through the tube.

These and other objects and features of the invention will be apparant from the following description when taken in conjunction with the accompanying drawings of which

BRIEF DESCRIPTION OF THE DRAWINGS

FIG. 1 is an exploded perspective view of an HPLC cartridge constructed in accordance with the present invention.

FIG. 2 is a cross-sectional view of the cartridge of FIG. 1 showing the details of construction thereof.

FIG. 3 is a cross section assembled view of cartridge constructed in accordance with the present invention as the same appears connected to a liquid chromatograph end fitting.

DETAILED DESCRIPTION OF THE PREFERRED EMBODIMENT

The cartridge of the present invention includes the following parts: the tube 10, the packing 12 disposed in a central bore 11 of the tube, end plugs 15,16, and frit filters 18,19. The end plugs and the filters are identical in construction respectively. All parts are cylindrical and axially symmetric. The tube 10 is elongate and is provided with a coaxial bore filled with the particulate packing 12 to form an elution column of predetermined length, in a known manner. The bore opens at each end into a seal recess including a flat bottom 22 transverse to the axis of the tube and a cylindrical outer wall 24. Each end plug is a short section of cylindrical shape and of a diameter which fits into the respective recess. The outer wall 26 of the plugs are raised slightly to form a pair of spaced circumferential ridges 28,29 which are dimensioned to achieve a partial interference fit with the wall as the plug is inserted so that the plug is difficult to remove upon disassembly of the device as has been encountered due to suction. Each seal plug is itself given a coaxial bore 30 which opens through a coaxial hollow chamber 31 at its inner end, (i.e., toward from the tube) into a frit retaining recess 32. The frit 18,19 is usually of small diameter (i.e., 3/32 inch). As shown in FIGS. 2 and 3, chamber 31 is shaped in the form of a frustum of a cone arranged to form a smooth transition from the smaller diameter of the bore 30, which is made the same as that of the inlet piping 36, to the diameter of the frit chamber 32, which is made the same as the diameter of the bore 11 of the column. The plug is longer than the depth of the sealed recess of the tube so as to extend beyond as indicated at 34 by an amount sufficient to accommodate its yielding and deformation under compression without allowing force to be developed directly in the tube itself as by being in contact with the tube ends or rims. The latter are free of contact and need not be sealed off.

The cartridge is assembled into an end fitting at each end as shown in FIG. 3. Such a fitting assembly includes an end fitting proper given the number 116 and end cap nut 122 into which a tubing supply line 36 from the liquid chromatograph is inserted and retained in place by a radial compression ferrule 140. A seal assembly 118 is contained within the end fitting by suitable means captured in the end of the end fitting itself as by retaining ring 158 bearing upon a positioning washer 159. The several parts of the assembly of the fitting are more fully described on co-pending application, Ser. No. 354,395 entitled High Pressure Seal and Coupling filed concurrently herewith, the detailed description and operation of which is incorporated by reference. Alternatively, the end fitting assembly may be of the type shown in the above referenced U.S. Pat. No. 4,313,828.

The present invention has been constructed to make microbore guard columns and analytical columns of exceedingly small internal diameter. Thus, the tube length may be of any effective amount within the usual parameters. At the extremes, guard column has been made in accordance with the present invention as short as 1 centimeter in length while an analytical column is common at nominal length of 22 centimeters. The internal diameter has now been reduced to 2 millimeters and may even be as low as 1 millimeter or one-half millimeter. Thus, the presently proposed column is standard in its exterior dimensions and sealing aspects, but may be made as small as user technology desires and manufacturing technology admits. The recess at each of the tube has an internal diameter of 0.220 inches while the end plug has an outer diameter of 0.215 inches and the ridges has an outer diameter of 0.224 inches. The frit is conventional centered stainless steel having a dimension of 3/32 inches.

Thus, there has been provided a new cartridge in which it is possible to achieve the advantages of microbore analytical columns covering a range of 0.5 millimeters to 2 millimeters internal diameter of conventional lengths. By so reducing the diameter of the column, the same separation efficiency can be obtained using a fourfold decrease in solvent volume while obtaining a multiple increase in sensitivity from the column. Lastly, columns of the type disclosed herein are connectable to other forms of detectors other than the standard detectors such spectrophotometers. Such other detectors include mass spectrometers and electrochemical detectors, both of which are mass per unit time sensitive so that the reduced flow will result in an even greater increase of sensitivity than what would be expected. To those skilled in the art to which this invention pertains, many adaptations and modifications will occur. Accordingly, the scope of the present invention is to be determined by reference to the accompanying claims, the drawings and the general principles given in this description and should not be limited by the specific numerical examples given except where indicated.

I claim:

1. In a high-pressure liquid chromatographic system, a replaceable column cartridge for carrying a packing, said cartridge comprising an elongate tube having a concentric bore therethrough, a packing of particulate material disposed in said bore, means forming enlarged first and second recesses concentrically with said bore and in alignment with the bore at each end of the tube, each such recess having a cylindrical sidewall of a diameter larger than the bore and an internally disposed flat bottom wall of annular shape, first and second generally cylindrical seal plugs each having opposing inner and outer parallel faces and dimensioned to slide in a close fit within each respective recess sidewalls and further dimensioned so that, when inserted into the end fitting of a liquid chromatograph, the plugs and cartridge form a self-suporting structure for containing the packing and each plug being adapted to be placed in end-to-end compression resisted solely by the plug surfaces bearing upon the bottom wall of each recess while confined by the recess sidewall, each plug being adapted to bear at its other end in sealed relation upon an end fitting.

2. The cartridge as in claim 1, further including a frit filter disposed in the bore of each said plug and concentrically therewith in the end facing toward said cartridge tube.

3. The cartridge as in claim 2 wherein said bore is of a diameter approximately the same as the feed piping of the chromatographic system, and the frit filter is of a diameter approximately the same as the cartridge bore, and further including transition means forming a continuous smooth transition between said diameters, said transition means having the shape of the frustum of a cone.

4. The high-pressure liquid chromatographic system as in claim 1 further including at least one circumferential ridge encircling and integrally formed with each plug to deform when placed into said recess, said ridge having a circumferential dimension slightly larger than said plug and the internal diameter of said recess.

5. The chromatographic system as in claim 1 in which said replaceable column cartridge plugs are made of polytetrafluroethylene.

6. The liquid chromatographic system as in claim 1 in which said bore in said column is of microbore dimensions and said plug is provided with a bore therein commensurate therewith.

* * * * *